United States Patent [19]
Le Febre

[11] Patent Number: 5,892,861
[45] Date of Patent: Apr. 6, 1999

[54] COATED OPTICAL WAVEGUIDES AS EXTREMELY LONG PATH SAMPLE CELLS

[75] Inventor: David A. Le Febre, Camino, Calif.

[73] Assignee: UOP LLC, Des Plaines, Ill.

[21] Appl. No.: 864,315

[22] Filed: May 28, 1997

[51] Int. Cl.⁶ .................................................. G02B 6/00
[52] U.S. Cl. .............................. 385/12; 385/13; 385/128; 250/227.11; 250/227.18
[58] Field of Search .............................. 385/12, 13, 122, 385/125, 127, 128; 65/403; 250/227.11, 227.18

[56] References Cited

U.S. PATENT DOCUMENTS

| 3,813,141 | 5/1974 | Miller | 350/96 |
| 4,834,496 | 5/1989 | Blyler, Jr. et al. | 385/12 |
| 4,962,996 | 10/1990 | Cuellar et al. | 385/128 |
| 5,315,672 | 5/1994 | Padovani | 385/12 |

*Primary Examiner*—Phan T. H. Palmer
*Attorney, Agent, or Firm*—Thomas K. McBride; Frank S. Molinaro

[57] ABSTRACT

A very long sample cell for spectrophotometric measurements can be used to extend sensitivity to very low levels of gaseous components, under about 50 parts per billion. The cell is an optical fiber positioned within the annular space of a housing, with a gas stream flowing along the annular space. The outer surface of the fiber is coated with a material, e.g., an adsorbent which concentrates at least one component of the gas stream at the interface of the fiber and annular space. An indispensable prerequisite is that the coating have a refractive index greater than that of the optical fiber core. Radiation is propagated along the core of the fiber, and the evanescent wave passes through the adsorbed component, ultimately changing the radiation detected at the output end of the fiber according to the nature and concentration of the component.

9 Claims, 1 Drawing Sheet

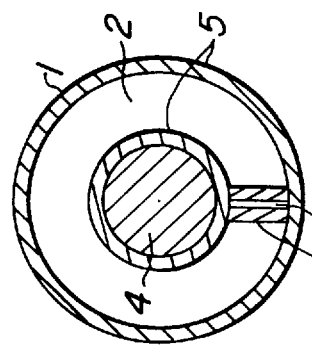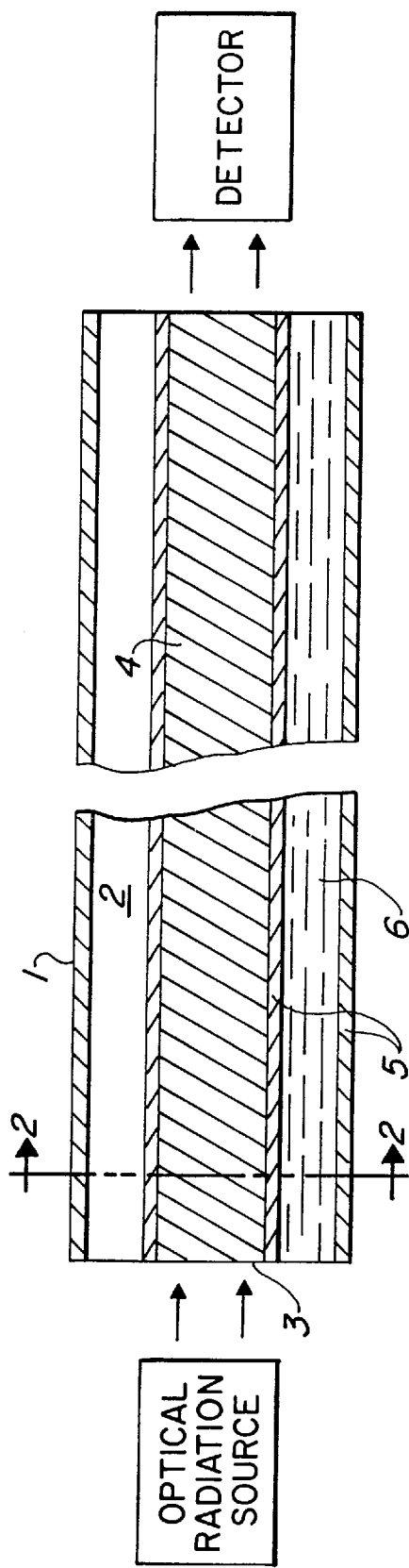

COATED OPTICAL WAVEGUIDES AS EXTREMELY LONG PATH SAMPLE CELLS

FIELD OF THE INVENTION

This invention relates to a sensor intended to detect very low levels of one or more components in a gas medium. More particularly, the invention relates to sensors which enable detection of components at levels as low as one part per trillion.

BACKGROUND OF THE INVENTION

In the specialty gas and semiconductor industries there currently are no primary measurement tools to determine very low concentrations of gas phase contaminants. By "very low concentration" is meant a concentration below about 50 parts per billion. Most existing techniques rely on gas standards to form a reference which then is correlated to a physical property of an immersed material. An example of this approach is the measurement of the bulk resistance of an adsorbent material, e.g., silicalite on a ceramic substrate. Moisture in a gas standard may be adsorbed on its surface, changing the resistance of the material. Using different concentrations of the adsorbed component generates a calibration curve which then is used to determine the concentration of the component in an unknown sample. The limitation in this approach lies at concentrations under about 50 parts per billion (ppb) where component adsorption on the walls of pressurized vessels confuses calibrations and where additional errors result from cross-contamination by other components having a similar effect on the physical property being measured. A further problem is associated with the long time constants involved in reaching equilibrium at very low concentrations of components, perhaps as long as several months at the parts per trillion (ppt) level.

A more sophisticated method of measurement is a long path length spectrometer. Knowing the path length and the molar adsorptivity of a component, an estimate of its concentration can be made without resorting to standards. However, the technique lacks sensitivity because the length of the path in, for example, infrared spectrophotometry is limited to about 25 meters, resulting in a lower sensitivity limit of several ppb. The technique also suffers from long time constants needed to achieve equilibrium. In the semiconductor industry, the preferred technique is the atmospheric pressure ionization mass spectrometer (APIMS), which has high specificity and high sensitivity allowing measurements to be made in the range of 100 parts per trillion (ppt). A disadvantage of this technique is the need for a primary standard for calibration, its high price, and the requirement of high gas flow. Response times also can be very long.

The present limitations may be exemplified using an industry standard instrument, namely, the Teledyne Model 8960 which is based on coulometric hygrometry and is stated to have a sensitivity of 0.5 ppb for water vapor. However, in measuring some ultra-dry streams, the instrument read −6 ppb for water content. This exemplifies the problems associated with standards as well as the limitation of one (representative) industry standard technique. The foregoing experience is a vivid demonstration that measuring components at very low levels in, for example, high purity gases used in semiconductor fabrication, is technically inadequate. Improvements in the technology for which the ultra-pure gas stream is used are limited by current analytical techniques. There is no need to cite an extensive list of gaseous components whose concentrations at under about 50 ppb need to be measured but cannot be done because of the presently inadequate analytical needs. The invention described within provides a solution to these needs. Even more importantly, it will be recognized from the ensuing description that our method, and the sensor employed in the application of our method, can be used for measuring concentrations far above the 50 ppb level which we define as the upper limit of "low level concentration" although it will be equally obvious to one skilled in the art that our method is most applicable to measuring concentrations under about 10 ppb.

What we have done is to construct an extremely long sample cell for spectrophotometric measurements using an optical waveguide, or optical fiber, as the underlying component. The optical fiber is mounted more or less concentrically within a second cylindrical structure. The resulting annular space serves to contain a flowing gas stream which contains at least one component whose measurement is desired. The optical fiber is clad with material, generally an adsorbent, which serves to adsorb the component being measured thus effectively creating a layer of the component at the interface of the optical fiber and annular space. Optical radiation is propagated along the fiber, and the evanescent wave associated with the optical radiation is then absorbed by the interfacial layer of the component to a degree relating to the concentration of the component in the flowing gas stream. Since absorption of wavelengths in the evanescent wave is characteristic of the material being adsorbed and continues along the length of the optical fiber, one has in effect a long sample cell, i.e., a cell whose length is that of the optical fiber itself. Thus, selected wavelengths of the optical radiation propagated in the optical fiber will be absorbed by the gaseous component present at the interfacial layer. The particular wavelengths absorbed will be characteristic of the component, and the amount of propagated light absorbed will be directly proportional to the concentration of the component at the interface. This method is particularly applicable to infrared and near infrared spectroscopy, although in principal it is limited only by the optical wavelengths which are efficiently propagated within optical fibers.

A significant, critical, and unexpected point of departure of our invention from prior art centers on the nature of the cladding, i.e., the coating on the surface of the optical fiber. Conventional wisdom states that the refractive index of the cladding must be less than the refractive index of the core in order for light to be propagated along the optical fiber. In contrast, an essential feature of our invention is that the cladding have a refractive index greater than that of the optical fiber! Consequently, one would not expect the sensors of our invention to propagate optical radiation. Furthermore, Maxwell's equations can be solved only for the case where the refractive index of the cladding is less than that of the optical fiber, which means that one can predict an evanescent wave for such a condition but one can not determine whether evanescent radiation would occur even if there were propagation of optical radiation along a fiber whose cladding had a refractive index greater than that of the fiber. In short, the present state of the art would not predict propagation of optical radiation along a fiber whose cladding had a refractive index greater than that of the fiber core, and even if radiation were propagated there would be no way to predict the presence of evanescent radiation in the cladding.

In the foregoing example, the cladding of the optical fiber was an adsorbent. However, there are cases where the component whose concentration is desired to be measured has no appreciable adsorption of the wavelengths being propagated within the optical fiber. In such cases the cladding could be a catalyst or a reactant leading to materials which would absorb wavelengths in the propagated radiation and therefore could be used as an effective analytical tool. Having stated that the cladding may differ depending upon the component to be measured as well as its optical adsorption properties, many variations of the foregoing will be apparent to those skilled in the art.

SUMMARY OF THE INVENTION

The purpose of this invention is to make available an extremely long sample cell for spectrophotometric measurements, a cell which is anticipated to be especially useful in determining gas phase concentrations under about 50 ppb, as well as providing a more general method of measuring components in gaseous streams regardless of their concentration. An embodiment of a large sample cell is an optical fiber coated with material, generally an adsorbent, whose refractive index is greater than that of the fiber, and positioned in the annular space of a second tube or shell. In a more specific embodiment, the adsorbent is a zeolite or a molecular sieve. In another embodiment, the coating material is a catalytic agent. Another aspect of our invention is a method of determining the concentration of the component in a gas stream by flowing the stream through the annular space of the aforementioned large cell, while propagating optical radiation through the optical fiber, and detecting the radiation exiting the fiber.

DESCRIPTION OF THE FIGURES

FIG. 1 is a longitudinal diagram of the long sample cell of this invention.

FIG. 2 is a transverse section taken along 2—2 of FIG. 1.

DESCRIPTION OF THE INVENTION

In one aspect our invention is an extremely long sample cell useful in measuring the concentration of a gaseous component in a gas stream. The cell is an optical fiber positioned, and usually more-or-less rigidly mounted, in the annular space of a shell surrounding the fiber. The optical fiber is coated with a material whose refractive index is greater than the core of the optical fiber itself and which interacts with at least one component; the coating material usually is an adsorbent, but it could be a catalytic agent or reactive agent in cases where the component has no appreciable absorption of the radiation being propagated along the fiber core. As previously stated, it is not only completely unexpected that an optical fiber coated with material having a refractive index higher than the fiber core will propagate radiation, but it is also contrary to conventional wisdom. In another aspect, our invention is a method of determining the concentration of at least one component in a gas stream by flowing the gas stream through the annular space of the aforementioned long sample cell. In the most usual case, one or more components are adsorbed by the adsorbent coating on the outside surface of the optical fiber, providing a very thin layer of adsorbed gaseous component at the interface of the fiber. An evanescent wave of the optical radiation propagated within the fiber will extend into the coating and be reflected into the core, and will be absorbed to a degree and at wavelengths characteristic of the adsorbed component. The very existence of such an evanescent wave can not be predicted from Maxwell's equations. By comparing the radiation exiting the optical fiber core in the presence of adsorbed component with the radiation exiting the fiber in the absence of the adsorbed component, one can obtain a measure of the concentration of the gaseous component in the gas stream.

FIG. 1 is a longitudinal diagram of a long sample cell and FIG. 2 is a transverse section of the same cell. We emphasize that many variants are possible as will be apparent to one with skill in the art. The description which follows will be in the context of the foregoing figures solely for ease and clarity of exposition, but it needs to be explicitly recognized that our invention is not limited thereto.

The heart of our invention is an optical fiber, 3, which serves as a waveguide for optical radiation of a range of frequencies or wavelengths used in the measuring process. At the input end of the optical fiber is the radiation source. The other end of the optical fiber is the output end at which is placed a detector. The detector measures the amount of light exiting the optical fiber at different wavelengths. The optical radiation propagated along the core, 4, of the fiber is of a wavelength or range of wavelengths necessarily used in the measurement of desired components. This aspect will become clearer in our subsequent description, but in general terms, typically will be in the infrared or near infrared region of the optical spectrum.

The optical fiber is positioned within the annular space, 2, of the shell or housing, 1, surrounding the fiber. A suitable housing very frequently will be a tube concentric with the optical fiber, although this is not a necessary limitation of the long cell. Rather, it merely reflects a convenient design. The housing may be the same or different material as the optical fiber, and again as a matter of convenience it frequently will be of the same material. Since optical fibers typically have a diameter of from 50 $\mu$M to about 500 $\mu$M, where the housing is a tube concentric with the optical fiber it will have a diameter on the order of 100 $\mu$M up through about 1000 $\mu$M. The foregoing dimensions are merely representative and are not critical to our invention.

The optical fiber is positioned within the annular space of the outer shell. Usually the optical fiber will be more or less rigidly mounted so as to be positioned within the annular space and U.S. Pat. No. 3,813,141 shows several variants which are possible. One type of simplified mounting is shown in FIG. 2, where the positioning means or supporting member, 6, is a strip perpendicular to the tangent of the shell and to the tangent of the optical fiber. The positioning means is firmly attached to both. In one variation the shell, optical fiber, positioning means or mounting strip are all the same material and the mounting strip is fused to the optical fiber and to the shell. We stress that the nature of the positioning means is unimportant; any means rigidly positioning the optical fiber within the annular space of the outer shell will suffice.

A key to our invention is that the coating, 5, placed on the outside surface of the optical fiber and which therefore forms an interface between the optical fiber and the annular space has a refractive index greater than that of the optical fiber core. For our invention to be operable, it is only the optical fiber which needs to be coated. However, because of the common methods of applying coatings, a selective coating of the optical fiber may be difficult, and it is more likely that the coating material will be on the inside surface of the shell as well as the surface(s) of the positioning means. The purpose of the coating is to concentrate components in the gas stream within the annular space at the interface of the optical fiber. This provides a layer of the gaseous component, or of another material derived from or related to the gaseous component to be measured, at the interface of the optical fiber.

The thickness of the coating is less than the wavelength of light that is needed to characterize the phenomena that is being observed. For example for water the preferred spectra to observe bound water in a molecular sieve is between 1850 and 2000 nm. Therefore the thickness should be less than 1850 nm, but this should also be adjusted for the opacity and scattering properties of the coating material and the number of modes propagating in the waveguide. The higher the opacity at a given range of wavelengths the lower the thickness and the higher number of modes the lower the thickness. Using an alumina based molecular sieve and a fused silica cross section of several hundred microns gives empirically a thickness of 100 to 200 nm.

For measuring oxygen, carbon dioxide or carbon monoxide the preferred spectrum is in the visible to near infrared (400 nm to 1600 nm), which generates a metal attenuation spectrum of rolling adsorption peaks of half widths that are several hundred nanometers wide and upon reaction with the analyte of interest generates lessor peaks to transparency. The change in the spectral signature describes which analyte is affecting the coating and the degree of the analytes' concentration. Multiple analytes reacting with the metal coating will generate complex spectra which must be deconvolved using suitable mathematical techniques. For metal coatings the reaction with analytes can be observed with coating thicknesses that are in the tens to hundreds of nanometers for a core diameter of several hundred microns.

The relationships between variables may perhaps be better understood with the help of the following comments. a) Analyte sensitivity is proportional to coating thickness but below the length of the wavelength of light used for analysis. Although multiple wavelength thicknesses can sense a measurable change in analyte concentration, a higher degree of attenuation results in the cell transmission. b) Analyte sensitivity is related to the optical changes that take place in the coating. Some coating reactions are slight and therefore the coating must be thicker to get a desired sensitivity. Porosity of the coating determines as well spectral attenuation but this is not well understood. c) Quantitation is achieved by determining the amount of gas or liquid contaminant (analyte) that has been in the presence of the coating. Therefore the flow of the gas or liquid stream must be known as well as the length of the cell, its temperature and the time interval between burnout. The measurement can be based on the rate of change of the spectrum and/or the total integral of the change over a fixed time.

The evanescent radiation travels into the thin coating of higher index of refraction. As the core decreases in diameter the greater is the evanescent radiation in the usual case. This may be calculated by applying a cylindrical coordinate system, making the cladding thickness infinite, then applying Maxwell's equations and trying to find a solution to the resulting differential equations. Applying a thin (less than a wavelength) coating of high index of refraction material to the core followed radially by a much lower index of refraction can not be solved, therefore this technique can not be mathematically modeled.

The number of coatings, subject to the requirement that they have a higher refractive index than the optical fiber core, spans most of inorganic chemistry. If one of the materials react or is adsorbed onto another and one is a gas, liquid or can flow in a stream (solid particles) and the second can be bonded to a glass then both become candidates for either the analyte to be sensed or the coating. There is an additional requirement that the reaction or adsorption between the analyte and the coating be reversible with temperature or pressure. However, there is an exception if the reaction is permanent but is optically small so that many reactions (measurements) can occur before the dynamic range of the instrument is saturated. There is a requirement for the coating to have a higher index of refraction than the core.

The two obvious classes of coatings are molecular sieves and metals. The analytes may be adsorbed onto (into) the molecular sieves and then desorbed by heating or through the application of a vacuum in the channel. Reaction with the metal surface yields oxides, nitrides, chlorides, fluorides, carbonyls, silicides, or any other reaction product which causes an optical change from the pure metal. The less obvious are amorphous coatings such as silicas or aluminas or polymeric materials (organic and inorganic).

Another approach is to coat the optical waveguide with a metal and then use techniques described in field flow fractionation to attract the material of interest to the metal coating which has a high potential applied to its surface. This would be suitable for biological materials and macromolecules, although it is unknown what spectral information would be derived.

The length of the cell is governed by the bulk optical attenuation of the optical waveguide. Theoretically the length could be in the 10s of kilometers, however a practical limitation as a cell is 100s of meters as limited by the permeability of the optical fiber itself (generally silica). This limitation is established by the travel time of the gas or liquid through the cell. For a 100 meter cell the travel time is in the several minute range for a gas.

Our invention is perhaps most readily exemplified by an adsorbent as a coating. The adsorbent then will provide a thin, interfacial layer of at least one of the components of a higher refractive index than the core of the optical fiber. There is propagated evanescent or imaginary radiation tens of wavelengths outside of the core and perpendicular to the direction of radiation travel within the core. Absorption of such evanescent radiation occurs at those wavelengths where the adsorbed component has characteristic spectral absorption, and unabsorbed radiation then is reflected back into the core and propagated along its longitudinal direction. The overall result of this process is that radiation is absorbed at selected wavelengths characteristic of the adsorbed component, corresponding to the absorption spectrum of the adsorbed component. Therefore, if the propagated radiation exiting the fiber in the presence of adsorbed component is compared with radiation exiting the fiber in the absence of the component, one obtains an absorption spectrum of the component. The degree of absorption will be proportional to the concentration of the adsorbed component (the adsorbate) at the interface, and thus provides a more-or-less absolute measurement of the adsorbate requiring no reference standards. However, the relation between adsorbate concentration and concentration of that component in the flowing gas stream still must be established via secondary standards; vide infra.

Although in principal radiation of any wavelength may be used, in practice the materials used in optical fibers limits the optical radiation largely to wavelengths of the ultraviolet, visible, and infrared regions, correspond roughly to 200–400 nm, 400–800 nm, and 800–3000,00 nm. The near infrared region, ca. 800–2500 nm, is of particular interest in the practice of this invention.

The analytical method which is another aspect of our invention follows quite simply from the description of the long cell given above. One has a gas stream containing at least one component which is to be measured, flowing within the annular space of the long cell described above. Acceptable flow rates are limited only by the frictional effects of gas flow, and consequently will be sensitively dependent upon the dimensions of the annular space. However, flow rates up to several mL per second are contemplated. Again, using adsorbents to exemplify the coating material, the flowing gas must be maintained in contact with the adsorbent for a sufficient time to establish equilibrium between the gaseous component to be measured in the vapor phase and the concentration of that same component present at the interface because of adsorption by the coating material. Contact times of between about tens of milliseconds to about 100s of seconds are contemplated to be necessary for the success of our invention. When equilibrium is established, optical radiation of appropriate wavelength(s) is inserted at the entrance of the optical fiber and the radiation exiting at the other end is determined using a suitable detector. By comparing the radiation characteristics—i.e., intensity at discrete wavelengths or wavelength regions—of radiation exiting in the presence of the adsorbed component with that exiting in the absence of the component one obtains a measure of both the nature of the component as well as its concentration at the interface, a concentration which is related to that in the flowing gas stream. For the purpose of our method, the component impurity in the flowing gas stream generally will be known, and it is its concentration which will be measured. However, it should be clear that at least in principle our invention can be used to simultaneously determine the nature of the component as well as its concentration.

As in any measurement system the basis of measurement is related to a physical property change. In this case the optical change in transmission spectra of the coating on the optical waveguide. The molar adsorptivity of, say water, when it is adsorbed by a molecular sieve causes the optical waveguide spectra to change. Below a certain concentration of water the spectra does not change. This is a very visible phenomena. This is also an absolute go no go measurement. The measurement floor is dictated by the design of the cell and the noise floor of the detector and electronics.

Partial pressures of the gas, partial pressure of the contaminants in the gas and the reaction kinetics of the coating determine what is measured. All measurement techniques have similar limitations, including an APIMS (atmospheric pressure ionization mass spectrometer). The APIMS is calibrated by using a gas mixing chamber which bleeds a contaminant into the gas stream in a known amount. This method is only accurate at high concentrations, i.e. 1 ppm and up. A slope is generated at high concentrations to predict the lower concentrations. An APIMS is believed to be a primary standard even though the mass spectrometer can not be directly calibrated from the ion concentration information. The extremely long sample cell does not suffer from a lack of calibration information. That information lies within the spectral information: a spectra exists that reflects on the amount of light passing through the coating (coating spectra) and the light passing through the captured analyte. This information reduces to a scaling problem which can be determined at a high, known concentration. In the ppb range and below there are no direct means of setting up standards—all the information is inferred from higher concentrations.

It is important for the success of our method that adsorption, or other phenomena occurring with the coating material, be reversible. Especially in those cases where the coating materials are zeolites and molecular sieves, it is expected that desorption of the various components will occur upon heating the long cell, especially in the presence of a flowing gas stream absent the measured component. Thus, it is anticipated that the long cell, once constructed, will be capable of reuse over many cycles.

I claim as my invention:

1. A sample cell for spectrophotometric determination of gaseous components in a flowing gas sample comprising:

a) a housing defining a volume of space for conducting the flowing gas sample;

b) an optical fiber positioned within said space defined by the housing;

c) a support for holding said optical fiber within said space; and d) a coating material having a refractive index greater than said optical fiber firmly adhering to the outer surface of said optical fiber and capable of interacting with at least one gaseous component of the flowing gas sample.

2. The sample cell of claim 1 wherein the coating is a zeolite, molecular sieve, or metal.

3. The sample cell of claim 1 wherein the coating is a catalyst or reactant capable of interacting with at least one gaseous component of the flowing gas sample.

4. The sample cell of claim 1 wherein the coating is an adsorbent capable of adsorbing at least one gaseous component of the flowing gas sample.

5. A method of analyzing the concentration of at least one component in a gas stream comprising:

a) inserting optical radiation into the core of an optical fiber positioned in an annular space of a hollow cylinder, said radiation being of a wavelength suitable for propagation along said optical fiber, said optical fiber being coated with an adsorbent effective to adsorb component being analyzed, said absorbent having a refractive index greater than said core of the optical fiber;

b) flowing said gas stream through said annular space at a flow rate and for a time effective for said adsorbent to adsorb said component;

c) measuring the intensity of the propagated optical radiation at at least one wavelength; and d) comparing said measured intensity with the intensity of propagated optical radiation of the same wavelength in the absence of said component.

6. An apparatus for spectrophotometric determination of gaseous components in a flowing gas sample comprising:

a) a housing defining a volume of space for conducting the flowing gas sample;

b) an optical fiber positioned within said space defined by the housing and having an input end and an output end;

c) a support for holding said optical fiber within said space;

d) a coating material having a refractive index greater than said optical fiber firmly adhering to the outer surface of said optical fiber and capable of interacting with at least one gaseous component in the flowing gas sample;

e) an optical radiation source in alignment with the input end of the optical fiber; and f) a detector in alignment with the output end of the optical fiber.

7. The apparatus of claim 6 wherein the coating is a catalyst or reactant capable of interacting with at least one gaseous component of the flowing gas sample.

8. The apparatus claim 6 wherein the coating is an adsorbent capable of adsorbing at least one gaseous component of the flowing gas sample.

9. The apparatus of claim 6 wherein the coating is a zeolite, molecular sieve, or metal.

* * * * *